United States Patent [19]

Cise et al.

[11] 4,132,848
[45] Jan. 2, 1979

[54] METHOD OF PREPARING A RAPIDLY DISSOLVING POWDER OF CRYSTALLINE CEPHALOTHIN SODIUM FOR PARENTERAL ADMINISTRATION

[75] Inventors: Michael D. Cise; Michael L. Roy, both of Indianapolis, Ind.

[73] Assignee: Eli Lilly and Company, Indianapolis, Ind.

[21] Appl. No.: 847,501

[22] Filed: Nov. 3, 1977

[51] Int. Cl.$^2$ ............................................. C07D 501/02
[52] U.S. Cl. ........................................ 544/28; 424/246
[58] Field of Search .................................. 544/30, 28

[56] References Cited
U.S. PATENT DOCUMENTS

| | | | |
|---|---|---|---|
| 4,028,355 | 6/1977 | Blackburn | 544/30 |
| 4,029,655 | 6/1977 | Cise | 544/20 |
| 4,061,853 | 12/1977 | Urech | 544/30 |

*Primary Examiner*—Nicholas S. Rizzo

*Attorney, Agent, or Firm*—Ralph W. Ernsberger; Arthur R. Whale; Leroy Whitaker

[57] ABSTRACT

Essentially crystalline cephalothin sodium for parenteral administration is prepared by a freeze-drying process wherein a ($C_1$–$C_3$ alcohol or acetone)-water solution of cephalothin sodium containing from about 2 to about 10 percent of $C_1$–$C_3$ alcohol or acetone by volume is chilled from room temperature to −20° C., or below, preferably about −40° C. over a 1–3 hour period and then warmed to from about −3° C. to about −10° C. and held for 3 hours or more, then cooled to −20° C., or below, preferably about −40° C., before subjecting said frozen solution to a high vacuum and a moderate amount of heat to sublime the frozen solvent therefrom. The resulting powder dissolves rapidly in acceptable pharmaceutical diluents. Alternatively, from about 2 to about 5 percent by weight of sodium bicarbonate, related to the amount of cephalothin sodium present, is added to the solution before freeze-drying.

18 Claims, No Drawings

METHOD OF PREPARING A RAPIDLY DISSOLVING POWDER OF CRYSTALLINE CEPHALOTHIN SODIUM FOR PARENTERAL ADMINISTRATION

BACKGROUND OF THE INVENTION

1. Field of Invention

This invention is directed to an improved freeze-drying (lyophilization) process. More specifically the instant invention concerns a freeze-drying process wherein cephalothin sodium for parenteral administration is prepared which is essentially crystalline and is rapidly soluble on reconstitution in a conventional acceptable pharmaceutical diluent and has excellent storage stability.

2. Prior Art

Freeze-drying is an old and often used process for removing a solvent from a solute. It provides a method for removing a solvent without damaging heat labile solutes. Antibiotics and other pharmaceuticals have been processed by freeze-drying procedures for three or more decades and foods, particularly instant coffee, have been prepared by this method for many years. Ordinarily, a solution from which it is desired to recover the solute in a relatively solvent-free state is frozen solid and then subjected to an environment of a high vacuum, and the temperature of the environment is raised to provide the units of heat absorbed in the sublimation of the frozen solvent. The temperature of the environment is kept below that which would result in the meltdown of the frozen solution. In practice, the temperature of the environment is coordinated with the vacuum to produce the highest reasonable sublimation rate, avoiding a melting of the frozen mass.

Water is the solvent generally utilized in a freeze-drying process. Other solvents or combinations thereof can be employed but are limited to those which become solid in the range of temperatures which can be employed practically in the process and which will sublime under vacuum.

Although all of the material does not have to be in solution to effectively operate a freeze-drying process, instant coffee being one probable example, this invention is concerned with a process wherein crystalline cephalothin sodium is prepared in a freeze-drying procedure from a true super-saturated solution. In freeze-drying antibiotics and other pharmaceuticals it has been the practice to follow the classic process outlined above; to wit, prepare solution, freeze to solid, subject to high vacuum, add heat, sublime solvent. However, when such a conventional procedure is followed, the process involving cephalothin sodium requires a cycle time of more than 24 hours to achieve a stable crystalline product.

The cephalothin sodium involved in this invention can be recovered from organic solvents, such as those identified above, in an essentially crystalline state. The crystals are equally as stable as the crystals prepared by the freeze-drying process of the instant invention.

However, recovering crystals of cephalothin sodium for use in ampoule preparations for parenteral administration poses other problems and conditions which are both inefficient, difficult and costly. For example, there is no effective way known to sterilize the crystals of cephalothin sodium recovered from organic solvents so the entire crystallization process must be carried out in an aseptic environment. In the large and extensive process required to sterilely crystallize cephalothin sodium there are many opportunities for the admittance of foreign materials into the crystals which later on will show up as particulate matter in a reconstituted ampoule of the antibiotic. No one has yet developed an apparatus for filling dry material into an ampoule which will measure the material going into each ampoule with as good a consistency and precision as can be routinely achieved with liquid filling equipment.

United States Patent Application, Ser. No. 744,552 now abandoned teaches and claims a novel and useful freeze-drying process for preparing crystalline cefazolin sodium for parenteral administration from an ethanol-water solution. Moreover, U.S. Pat. No. 4,029,655 describes a process which embodies a procedure that includes a very rapid cooling of an aqueous solution to nucleate the cephalothin sodium, among other cephalosporins, during the interval that the freezing takes place. Such nucleation crystallizes the bulk of the cephalothin sodium from the solution immediately prior to the solidification of the water. Consequently, when the sublimation procedure is initiated the cephalothin sodium already exists as crystals and does not depend on the crystallization to take place as the solvent is removed. The solvent is sublimed away and the cephalothin sodium remains behind.

While the process provides a means for obtaining stable sterile crystalline cephalothin sodium for parenteral administration, the process requires more than 24 hours for the completion of one cycle. Consequently, the scheduling of the use of the freeze-drying equipment and the work schedules of the personnel is unsatisfactory because of the irregularity of the operation. Following the teachings of the prior art requires a 28 to 36 hour cycle from the starting of the freeze-drying operation until it is completed. This relatively long time is a source of added cost to the product and annoyance and irritation to the personnel.

Accordingly, it is an object of this invention to provide a process of freeze-drying cephalothin sodium that will result in essentially crystalline powder for reconstitution for parenteral administration and which will permit the turn-around of the freeze-drying equipment every 24 hours or less.

Another object of this invention is to provide a process which will include the liquid filling of a measured volume of a sterile solution of a known concentration of cephalothin sodium into an ampoule wherein such cephalothin sodium is recovered from such solution as an essentially crystalline material for reconstitution for parenteral administration which is storage stable.

Still another object of this invention is to provide an ampoule containing an essentially crystalline cephalothin sodium which is storage stable and which upon reconstitution for parenteral administration is substantially free of foreign particulate matter.

SUMMARY

Now it has been discovered that a storage stable, essentially crystalline cephalothin sodium for reconstitution for parenteral administration can be prepared by a freeze-drying procedure requiring less than 24 hours comprising the following steps: (a) cephalothin sodium is dissolved in a solvent system comprised of from about 2 to about 10 percent by volume of a $C_1$–$C_3$ alcohol or acetone and from about 98 to about 90 percent by volume of water in a concentration of between about 20 and about 40 percent (w/w). (b) The cephalothin sodium preparation from (a) is cooled rapidly to a temperature of about −20° C. or below, preferably about −40° C. (c) The temperature of the cephalothin sodium preparation from (b) is then warmed to between about −3° C. and about −10° C. (d) The cephalothin sodium preparation from (e) is held between about −3° C. and about −10° C. for 3 hours or more. (e) The cephalothin sodium preparation from (d) is cooled to about −20° C. or below, preferably about −40° C. and subjected to an environment in which the pressure is maintained at a maximum of 1 mm absolute. And, (f) the temperature of the environment in which the cephalothin sodium preparation from (e) is maintained at a maximum of 1 mm absolute is raised to 50° C. or below, subliming the solvent from the cephalothin sodium preparation resulting in the recovery of an essentially crystalline cephalothin sodium having a moisture content of not more than 1.0 percent, and a $C_1$–$C_3$ alcohol or acetone content of not more than 1.0 percent.

DESCRIPTION OF THE PREFERRED EMBODIMENTS

The useful process of the present invention comprises a procedure utilizing a freeze-drying operation wherein from about 20 to about 40 percent (w/w) of cephalothin sodium is dissolved in a solvent system comprised of from about 2 to about 10 percent $C_1$–$C_3$ alcohol or acetone and from about 98 to about 90 percent water. Such a solution is achieved by heating the solution to a temperature of up to 70° C. to effect complete solubilization. The resulting solution can be sterilized by filtration is desired. The solution is then exposed to an environment in which the solution is cooled rapidly to a temperature of about −20° C. or below, preferably about −40° C. The cooling period may be completed in from 1 to 3 hours.

After the rapid cooling to about −20° C. or below, preferably about −40° C., the frozen solution is warmed to between about −3° C. and about −10° C. and held at such temperature for 3 hours, or more, to assure complete crystallization.

Once the frozen solution has been held at about −3° C. to about −10° C. for 3 hours or more, it is again cooled to −20° C. or below, preferably about −40° C.

Following the critical steps just described, a conventional freeze-drying operation is employed to sublime the ice, leaving cephalothin sodium crystals having a moisture content of not more than 1 percent and a $C_1$–$C_3$ alcohol or acetone content of not more than 1 percent. Such crystals have a suitable storage stability of three years or more at room temperature, and dissolve in one minute or less in an acceptable pharmaceutical diluent in concentrations appropriate for parenteral administration. The improvement in the freeze-drying rate of the cephalothin sodium prepared by the process described above over the conventionally prepared cephalothin sodium crystals freeze-dried from an aqueous solution results in from about a 15 to about a 50 percent reduction in the time required to complete the freeze-drying cycle.

The crux of the instant invention is found in the combination of the use of the ($C_1$–$C_3$ alcohol or acetone)-water solvent system and the establishment of a supersaturated solution of cephalothin sodium contained in such a solvent system, and the rapid cooling of the solution to −20° C. or below, preferably about −40° C. The presence of the $C_1$–$C_3$ alcohol or acetone in the solvent system acts as an anti-solvent and reduces the solubility of the cephalothin sodium. It was discovered that the cephalothin sodium is substantially less soluble in a ($C_1$–$C_3$ alcohol or acetone)-water solvent than in water alone. Consequently, by warming the frozen solution to from about −3° C. to about −10° C. the nucleation and crystallization can be completed in 3 hours or slightly more as compared to the 14 to 20 hours required when no alcohol or acetone is used.

In one aspect of the present invention a rapidly soluble, essentially crystalline, cephalothin sodium for reconstitution for parenteral administration is prepared by a method comprised of the following steps: (a) cephalothin sodium is dissolved in a ($C_1$–$C_3$ alcohol or acetone)-water solvent. (b) The cephalothin sodium solution/suspension from (a) is heated to a temperature up to about 70° C. to assure a complete solution, and, if desired, can be filtered through a sterilizing filter into a previously sterilized container. (c) The preparation from (b) is cooled rapidly to about −20° C., or below, preferably about −40° C., over a period of from about 1 to about 3 hours. (d) The preparation from (c) is warmed to a temperature of from about −3° C. to about −10° C. (e) The preparation from (d) is held at a temperature in the range of (d) for 3 hours, or more. (f) The frozen solution from (e) is cooled to about −20° C., or below, preferably about −40° C. (g) The preparation from (f) is subjected to an environment wherein the pressure is maintained at a maximum of no more than 1 mm absolute. (h) The temperature of the environment in which the preparation from (g) is exposed is raised to a maximum of about 50° C., avoiding the melting of such preparation. And, (i) the frozen solvent is sublimed from the preparation from (h) until the resulting crystals of cephalothin sodium have a moisture content of not more than 1 percent, and an a $C_1$–$C_3$ alcohol or acetone content of not more than 1 percent.

The ($C_1$–$C_3$ alcohol or acetone)-water solvent employed in the useful method of this invention can contain from about 2 to about 10 percent of a $C_1$–$C_3$ alcohol or acetone and from about 98 to about 90 percent water (v/v). The preferred solvent system is comprised of from about 3 to about 5 percent by volume of a $C_1$–$C_3$ alcohol or acetone and about 97 to about 95 percent by volume of water. In practice the cephalothin sodium is dissolved preferably in the water and a volume of a $C_1$–$C_3$ alcohol or acetone, preferably 95 percent ethanol, equal to 4 percent of the volume of the solution of the cephalothin sodium, is added to such solution.

A concentration of cephalothin sodium of from about 20 to about 40 percent w/w in the $C_1$–$C_3$ alcohol- or acetone-water solvent is satisfactory for developing the large crystals on freeze-drying. The preferred range is from about 25 to 35 percent w/w. Especially preferred is a 30 percent (w/w) solution of cephalothin sodium. In practice, one especially preferred concentration of cephalothin sodium is provided by dissolving 30 gm of cephalothin sodium in water q. s'd. to 100 grams and adding thereto 3.55 ml of 95 percent gain alcohol, making a solution containing about 29 percent (w/w) of the solute.

Sterilization of ($C_1$–$C_3$ alcohol or acetone)-water solution of cephalothin sodium can be achieved by filtering such solution through sterile filtering means known to those skilled in the art and collecting the filtrate in a previously sterilized container. Illustratively, sterile filtering can be effected using a heat sterilized plate and frame filter press equipped with an asbestos pad, or a filtering membrane of cellulose acetate or nitrate, or a candle having a porosity below 0.22 μm.

The rapid cooling of the ($C_1$–$C_3$ alcohol or acetone)-water solution of cephalothin sodium can be best accomplished by exposing such solution to an environment of about −40° C. The temperature of the solution can be determined by locating a thermocouple approximately in the center of the solution to indicate the temperature at that point. Continued experience with the actual apparatus used to accomplish the lowering of the temperature will provide more useful information as to the operating characteristics which should be followed to meet the processing parameters specified. This is so because of the wide variation in the design and operation of different freeze-dryers.

When the −20° C., or lower, preferably −40° C. temperature has been reached following the method outlined above, the frozen solution is warmed to about −3° C. to about −10° C. to initate the nucleation and crystallization of the cephalothin sodium. The frozen solution is held at a temperature in that range for a period of about 3 hours or more to complete the crystallization.

After such period of holding at from about −3° C. to about −10° C., the frozen solution is again chilled to about −20° C. or below, preferably about −40° C., to complete solidification. No apparent benefit was found in holding the frozen mass at −20° C. or below, preferably about −40° C. after solidification was complete. At this point essentially all of the cephalothin sodium is present in the frozen mass as free crystals. A conventional freeze-drying operation is then utilized to sublime the solvent from the frozen mass leaving a deposit of essentially crystalline cephalothin sodium.

The frozen cephalothin sodium preparation wherein the nucleation of the crystals is substantially complete is subjected to an environment where the pressure can be reduced to a practical maximum of no more than 1 mm mercury absolute. It is preferable to reduce the pressure much more than to 1 mm mercury absolute. The best results are obtained with an absolute pressure of between about 0.05 mm and 0.2 mm. This latter pressure range is ordinarily readily attainable in both laboratory and commerical freeze-drying apparatus, the design, construction and operation of which are all well known to those skilled in the art. After the pressure of the environment described above has been reduced to an operating level, heat is introduced into such an environment. The temperature of the environment is raised to a point where the maximum sublimation rate can be achieved without melting the frozen mass. As a general rule, the temperature and the pressure are inversely related; the more effective the pressure reduction, the higher the temperature which can be employed in the subliming operation. As a common guide it can be said that a maximum environment temperature of 50° C. can be reached with a highly efficient vacuum system where the absolute pressure is maintained at about 0.05 mm absolute (50 μm). In any event, the temperature should be raised slowly so as to avoid overloading the pressure-reducing system which can produce an undesirable melting of the frozen mass. Preferably, the temperature of the environment in the sublmining operation should be maintained between about 10° C. and about 40° C. with the pressure held at or below 0.2 mm absolute.

Subliming of the ice from the frozen mass is continued until the moisture content of the cephalothin sodium crystals is below 1 percent and the $C_1$–$C_3$ alcohol or acetone content is below 1 percent. Such a specification assures physical stability of the resulting crystals. Cephalothin sodium does not crystallize as a hydrate.

The cephalothin sodium prepared as detailed above is essentially crystalline. For example, physical analyses of cephalothin sodium indicated a crystallinity of between 92 and 100 percent. In any event, a sufficiently high amount of crystallinity was obtained to impart storage stability; i.e., an absence of a yellowing of the substance and loss of microbiological potency for up to 3 years at room temperature. When the process is operated to include the sterile filtering of the cephalothin sodium solution and the freeze-drying is done under aseptic conditions the cephalothin sodium crystals can be sterile filled into previously sterilized ampoules in appropriate quantities for reconstitution for parenteral administration.

In another aspect of this invention the procedure outlined and discussed in detail hereinbefore is augmented by an additional step which comprises filling a measured volume of the ($C_1$–$C_3$ alcohol or acetone)-water solution after suitable sterile filtration into a previously sterilized ampoule, such measured volume containing the quantity of cephalothin sodium which is desired in such ampoule after the freeze-drying operation. The ampoules containing the ($C_1$–$C_3$ alcohol or acetone)-water solution of cephalothin sodium are then processed in the same manner as described above. The resulting freeze-dried cephalothin sodium ampoule is ready for sterile stoppering and capping.

In practice it is preferred to sterile fill a measured volume of sterile ($C_1$–$C_3$ alcohol or acetone)-water cephalothin sodium solution into a previously sterilized ampoule as at least two beneficial results are obtained. First, a more precise and consistent quantity of the cephalothin sodium can be filled into an ampoule in the liquid form than in the solid (crystals) form. And, second, it is much easier to achieve and maintain sterile operating conditions in liquid filling operations than in dry filling operations. Moreover, air pollution is less of a problem when handling liquids than dry materials.

Alternatively, a quantity of sodium bicarbonate, equal to from about 2 to about 5 percent, preferably about 3 percent, of the cephalothin sodium can be added to the cephalothin solution before sterile filtration. Such an addition provides a crystalline cephalothin sodium which after reconstitution will have approximately a neutral pH, helping to reduce the stinging experienced on I.M. administration.

The instant invention is further illustrated by the following examples.

PROCEDURE I

Five hundred grams of cephalothin sodium having a moisture content of about 1 percent were dissolved in 1166.6 grams of water for injection, U.S.P.

The resulting water solution of cephalothin sodium was warmed to 62° C. to complete solution and filtered through a 0.45 μm Millipore membrane into an appropriate vessel.

The resulting aqueous solution containing 30 percent cephalothin sodium (w/w) was used in 50 ml. aliquots in the following examples.

EXAMPLE I

Fifty milliliters of the 30 percent (w/w) cephalothin sodium solution was combined with 2 ml. of 95% grain alcohol (equivalent to 4% v/v).

The ethanol-water solution of cephalothin sodium was filled into previously sterilized vials in an amount of about 3.56 ml. per vial. The quantity of solution was calculated to provide 1 gram ampoules of cephalothin sodium.

The filled vials were placed in a conventional freeze-drying unit and the temperature of the solution was lowered rapidly to about −35° C. over a period of less than 3 hours and then the temperature was warmed to about −7° C. as quickly as possible. The vials were held for 3 hours plus after the frozen mass had reached a temperature of about −7° C.

Then the vials were cooled to about −35° C. after being held for a little more than 3 hours at −7° C.

The pressure is the freeze-dryer was reduced to below 0.2 mm mercury absolute and the temperature was raised to about 10° C. for the sublimation of the ethanol-water solvent. Eventually the temperature was raised to 25° C. taking care not to melt the frozen mass in the vials. When the sublimation process was completed, the vacuum was released and the resulting vials were tested for moisture content, ethanol content and reconstitution time.

Typical moisture content on individual vials was 0.10 and 0.11 percent.

Two vials tested for ethanol residue showed less than 0.5 percent.

Five vials examined for reconstitution time required between 30 and 60 seconds to dissolve the cephalothin sodium in 4.0 ml. of water for injection, U.S.P.

EXAMPLE II

Two milliliters of methanol were added to 50 ml. of the 30 percent (w/w) cephalothin sodium solution from Procedure I. (Equivalent to 4% v/v).

The methanol-water solution of cephalothin sodium was filled into previously sterilized vials in an amount of about 3.56 ml. per vial. The quantity of solution was calculated to provide 1 gram ampoules of cephalothin sodium.

The filled vials were placed in a conventional freeze-drying unit and the temperature of the solution was lowered rapidly to about −35° C. over a period of less than 3 hours and then the temperature was warmed to about −7° C. as quickly as possible. The vials were held for 3 hours plus after the frozen mass had reached a temperature of about −7° C.

Then the vials were cooled to about −35° C. after being held for a little more than 3 hours at −7° C.

The pressure in the freeze-dryer was reduced to below 0.2 mm mercury absolute and the temperature was raised to about 10° C. for the sublimation of the methanol-water solvent. Eventually the temperature was raised to 25° C. taking care not to melt the frozen mass in the vials. When the sublimation process was completed, the vacuum was released and the resulting vials were tested for moisture content, methanol content and reconstitution time.

Typical moisture content on individual vials was 0.10 and 0.11 percent.

Two vials tested for methanol residue showed less than 0.5 percent.

Five vials examined for reconstitution time required between 30 and 60 seconds to dissolve the cephalothin sodium in 4.0 ml of water for injection, U.S.P.

EXAMPLE III

Acetone in a volume of 2.0 ml. was added to 50 ml. of the 30 percent (w/w) cephalothin sodium solution from Procedure I. (Equivalent to 4% (v/v)).

The acetone-water solution of cephalothin sodium was filled into previously sterilized vials in an amount of about 3.56 ml. per vial. The quantity of solution was calculated to provide 1 gram ampoules of cephalothin sodium.

The filled vials were placed in a conventional freeze-drying unit and the temperature of the solution was lowered rapidly to about −35° C. over a period of less than 3 hours and then the temperature was warmed to about −7° C. as quickly as possible. The vials were held for 3 hours plus after the frozen mass had reached a temperature of about −7° C.

Then the vials were cooled to about −35° C. after being held for a little more than 3 hours at −7° C.

The pressure in the freeze-dryer was reduced to below 0.2 mm mercury absolute and the temperature was raised to about 10° C. for the sublimation of the acetone-water solvent. Eventually the temperature was raised to 25° C. taking care not to melt the frozen mass in the vials. When the sublimation process was completed, the vacuum was released and the resulting vials were tested for moisture content, acetone content and reconstitution time.

Typical moisture content on individual vials was 0.10 and 0.11 percent.

Two vials tested for acetone residue showed less than 0.5 percent.

Five vials examined for reconstitution time required between 30 and 60 seconds to dissolve the cephalothin sodium in 4.0 ml of water for injection, U.S.P.

EXAMPLE IV

Two and one-half milliliters of isopropanol were added to 50 ml. of the 30 percent (w/w) cephalothin sodium solution from Procedure I. (Equivalent to 5% v/v).

The isopropanol-water solution of cephalothin sodium was filled into previously sterilized vials in an amount of about 3.6 ml. per vial. The quantity of solution was calculated to provide 1 gram ampoules of cephalothin sodium.

The filled vials were placed in a conventional freeze-drying unit and the temperature of the solution was lowered rapidly to about −35° C. over a period of less than 3 hours and then the temperature was warmed to about −7° C. as quickly as possible. The vials were held for 3 hours plus after the frozen mass had reached a temperature of about −7° C.

Then the vials were cooled to about −35° C. after being held for a little more than 3 hours at −7° C.

The pressure in the freeze-dryer was reduced to below 0.2 mm mercury absolute and the temperature was raised to about 10° C. for the sublimation of the isopropanol-water solvent. Eventually the temperature was raised to 25° C. taking care not to melt the frozen mass in the vials. When the sublimation process was completed, the vacuum was released and the resulting vials were tested for moisture content, isopropanol content and reconstitution time.

Typical moisture content on individual vials was 0.10 and 0.11 percent.

Two vials tested for isopropanol residue showed less than 0.5 percent.

Five vials examined for reconstitution time required between 30 and 60 seconds to dissolve the cephalothin sodium in 4.0 ml of water for injection, U.S.P.

EXAMPLE V

A total of 10.657 grams of sodium bicarbonate were dissolved in 954 grams of water for injection U.S.P. and cooled to 5° C. Three hundred and seventy-five grams of cephalothin sodium were added with stirring and the solution was heated to 66.5° C. to complete the dissolution of the cephalothin sodium. The resulting solution was filtered through a 45 μm membrane.

Eleven hundred milliliters of the filtrate were collected and 44 ml. of 95% grain alcohol added thereto. The concentration of cephalothin sodium was 28 percent (w/w) and the ethanol 4 percent (v/v).

The ethanol-water solution of cephalothin sodium was filled into previously sterilized vials in an amount of about 3.75 ml. per vial. The quantity of solution was calculated to provide 1 gram ampoules of cephalothin sodium.

The filled vials were placed in a conventional freeze-drying unit and the temperature of the solution was lowered rapidly to about −35° C. over a period of less than 3 hours and then the temperature was warmed to about −7° C. as quickly as possible. The vials were held for 3 hours plus after the frozen mass had reached a temperature of about −7° C.

Then the vials were cooled to about −35° C. after being held for a little more than 3 hours at −7° C.

The pressure in the freeze-dryer was reduced to below 0.2 mm mercury absolute and the temperature was raised to about 10° C. for the sublimation of the ethanol-water solvent. Eventually the temperature was raised to 25° C. taking care not to melt the frozen mass in the vials. When the sublimation process was completed, the vacuum was released and the resulting vials were tested for moisture content, ethanol content and reconstitution time.

Typical moisture content on individual vials was 0.10 and 0.11 percent.

Two vials tested for ethanol residue showed less than 0.5 percent.

Five vials examined for reconstitution time required between 30 and 60 seconds to dissolve the cephalothin sodium in 4.5 ml. of water for injection, U.S.P.

What is claimed is:

1. A method of preparing essentially crystalline cephalothin sodium for reconstitution for parenteral administration by a freeze-drying process requiring less than 24 hours comprising the steps of:
   (a) dissolving said cephalothin sodium in a solvent comprised of from about 2 to about 10 percent of a $C_1$–$C_3$ alcohol or acetone and from about 98 to about 90 percent water (v/v);
   (b) cooling the solution from (a) to about −20° C. or below;
   (c) warming the preparation from (b) to a temperature of between about −3° C. and about −10° C.;
   (d) maintaining the temperature of the preparation from (e) at from about −3° C. to about −10° C. for a period of 3 hours or more;
   (e) cooling the preparation from (d) to about −20° C., or below;
   (f) reducing the pressure of the environment in which the preparation from (e) is maintained to a maximum of 1 mm of mercury absolute;
   (g) raising the temperature of the environment in which the preparation from (f) is maintained to a maximum of 50° C., avoiding the melting of such preparation; and
   (h) subliming the solvent from the preparation from (g) until the resulting crystals of said cephalothin sodium have a moisture content of not more than 1.0 percent, and a $C_1$–$C_3$ alcohol or acetone content of not more than 1.0 percent.

2. The method according to claim 1 wherein the $C_1$–$C_3$ alcohol or acetone content of the ($C_1$–$C_3$ alcohol or acetone)-water solution of cephalothin sodium is about 4 percent (v/v).

3. The method according to claim 1 wherein the concentration of the cephalothin sodium in the ($C_1$–$C_3$ alcohol or acetone)-water solution is between about 20 and about 40 percent (w/w).

4. The method according to claim 3 wherein the concentration of cephalothin sodium is between about 25 and about 35 percent (w/w).

5. The method according to claim 3 wherein the concentration of cephalothin sodium is about 30 percent (w/w).

6. The method according to claim 1 wherein the pressure is reduced to between about 0.05 and about 0.20 mm of mercury absolute (50 to 200 μm absolute) and the temperature of the environment is raised slowly to between about 0° C. and about 50° C. maintaining an absolute pressure of no more than 0.20 mm. of mercury avoiding the melting of said cephalothin sodium preparation.

7. A method of preparing an ampoule of sterile, essentially crystalline cephalothin sodium for reconstitution for parenteral administration by a freeze-drying process requiring less than 24 hours comprising the steps of:
   (a) dissolving said cephalothin sodium in a solvent comprised of from about 2 to about 10 percent of a $C_1$–$C_3$ alcohol or acetone and from about 98 to about 90 percent water (v/v);
   (b) filtering the solution from (a) through a sterilizing filter into a previously sterilized container;
   (c) filling a volume of the sterile solution from (b) into a previously sterilized ampoule such that the quantity of solute therein is the amount of said cephalothin sodium desired in said ampoule;
   (d) cooling the filled ampoule from (c) rapidly over a period of from 1 to about 3 hours from room temperature to about −20° C., or below;
   (e) warming the ampoule from (d) to a temperature from about −3° C. to about −10° C.;
   (f) maintaining the temperature of the ampoule from (e) at about −3° C. to about −10° C. for a period of about 3 hours or more;
   (g) cooling the ampoule from (f) to about −20° C., or below;
   (h) reducing the pressure of the environment in which the ampoule from (g) is maintained to a maximum of 1 mm of mercury absolute;
   (i) raising the temperature of the environment in which the ampoule from (h) is maintained to a maximum of 50° C., avoiding the melting of the contents of such ampoule; and
   (j) subliming the solvent form the preparation from (i) until the resulting crystals of said cephalothin sodium have a moisture content of not more than 1.0 percent and a $C_1$–$C_3$ alcohol or acetone content of not more than 1.0 percent.

8. The method according to claim 7 wherein the $C_1$–$C_3$ alcohol or acetone content of the solution of cephalothin sodium is about 4 percent (v/v).

9. The method according to claim 8 wherein the concentration of the cephalothin sodium in the ($C_1$–$C_3$ alcohol or acetone)-water solution is between about 20 and about 40 percent (w/w).

10. The method according to claim 9 wherein the concentration of cephalothin sodium is between about 25 and about 35 percent (w/w).

11. The method according to claim 9 wherein the concentration of cephalothin sodium is about 30 percent (w/w).

12. The method according to claim 7 wherein the pressure is reduced to between about 0.05 and about 0.20 mm of mercury absolute (50 to 200 $\mu$m absolute) and the temperature is raised slowly to between about 0° C. and about 50° C. maintaining an absolute pressure of no more than 0.20 mm of mercury avoiding the melting of said cephalothin sodium preparation.

13. A method of preparing an ampoule of sterile, essentially crystalline cephalothin sodium for reconstitution of parenteral administration by a freeze-drying process requiring less than 24 hours comprising the steps of:
   (a) dissolving said cephalothin sodium in a solvent comprised of from about 2 to about 10 percent of a $C_1$–$C_3$ alcohol or acetone and from about 98 to about 90 percent water (v/v).
   (b) commingling from about 2 to about 5 percent, relative to the amount of cephalothin sodium present, of sodium bicarbonate with the solution from (a);
   (c) filtering the solution from (b) through a sterilizing filter into a previously sterilized container;
   (d) filling a volume of the sterile solution from (c) into a previously sterilized ampoule such that the quantity of solute therein is the amount of said cephalothin sodium desired in said ampoule;
   (e) cooling the fluid ampoule from (d) rapidly over a period of from 1 to about 3 hours from room temperature to about −20° C., or below;
   (f) warming the ampoule from (e) to a temperature from about −3° C. to about −10° C.;
   (g) maintaining the temperature of the ampoule from (f) from −3° C. to about −10° C. for a period of from 3 hours or more;
   (h) cooling the ampoule from (g) to about −20° C., or below;
   (i) reducing the pressure of the environment in which the ampoule from (h) is maintained to a maximum of 1 mm of mercury absolute.
   (j) raising the temperature of the environment in which the ampoule from (e) is maintained to a maximum of 50° C., avoiding the melting of the contents of such ampoule; and
   (k) subliming the solvent from the preparation from (j) until the resulting crystals of said cephalothin sodium, have a moisture content of not more than 1.0 percent and $C_1$–$C_3$ alcohol or acetone content of not more than 1.0 percent.

14. The method according to claim 13 wherein the $C_1$–$C_3$ alcohol or acetone content of the ($C_1$–$C_3$ alcohol or acetone)-water solution of cephalothin sodium is about 4 percent.

15. The method according to claim 14 wherein the concentration of the cephalothin sodium in the ($C_1$–$C_3$ alcohol or acetone)-water solution is between about 20 and about 40 percent (w/w).

16. The method according to claim 15 wherein the concentration of cephalothin sodium is between about 25 and about 35 percent (w/w).

17. The method according to claim 15 wherein the concentration of cephalothin sodium is about 30 percent (w/w).

18. The method according to claim 13 wherein the pressure is reduced to between about 0.05 and about 0.20 mm of mercury absolute (50 to 200 $\mu$m absolute) and the temperature is raised slowly to between about 0° C. and about 50° C. maintaining an absolute pressure of no more than 0.20 mm of mercury avoiding the melting of said cephalothin sodium preparation.

* * * * *